United States Patent [19]

Drake

[11] Patent Number: 5,223,231

[45] Date of Patent: Jun. 29, 1993

[54] APPARATUS FOR STERILIZING MEDICAL WASTE BY MICROWAVE AUTOCLAVING

[76] Inventor: Robert C. Drake, 123 Darcy Cir., Islip, N.Y. 11751

[21] Appl. No.: 803,461

[22] Filed: Dec. 6, 1991

[51] Int. Cl.$^5$ .................. A61L 11/00; G01D 11/00
[52] U.S. Cl. .................. 422/297; 422/295; 422/119; 422/21; 422/26; 588/227
[58] Field of Search .................. 422/21, 22, 26, 119, 422/295, 297, 300, 302, 307, 301; 588/227, 900

[56] References Cited

U.S. PATENT DOCUMENTS

| | | | |
|---|---|---|---|
| 3,880,586 | 4/1975 | Murayama et al. | 209/11.5 |
| 3,885,915 | 5/1975 | Utsumi et al. | 426/241 |
| 3,926,556 | 12/1975 | Boucher | 426/241 |
| 3,955,286 | 5/1976 | Anrep | 34/1 |
| 4,223,512 | 9/1980 | Buchner | 53/425 |
| 4,250,139 | 2/1981 | Luck et al. | 422/21 |
| 4,331,633 | 5/1982 | Lathrop, Jr. | 422/26 |
| 4,351,091 | 9/1982 | Goodkin | 27/22 R |
| 4,393,088 | 7/1983 | Matsusaka | 426/234 |
| 4,400,401 | 8/1983 | Beauvais et al. | 426/234 |
| 4,406,860 | 9/1983 | Beauvais et al. | 422/113 |
| 4,406,861 | 9/1983 | Beauvais et al. | 422/113 |
| 4,599,216 | 7/1986 | Rohrer et al. | 422/21 |
| 4,614,514 | 9/1986 | Carr et al. | 604/113 |
| 4,670,227 | 6/1987 | Smith et al. | 422/297 |
| 4,671,935 | 6/1987 | Rohrer et al. | 422/21 |
| 4,839,142 | 6/1989 | Charm | 422/21 |
| 4,839,485 | 6/1989 | Koch et al. | 219/10.55 A |
| 4,896,010 | 1/1990 | O'Conner et al. | 219/10.55 M |
| 4,935,114 | 6/1990 | Varma | 204/157.43 |
| 4,956,155 | 9/1990 | Rohrer et al. | 422/297 |
| 4,971,773 | 11/1990 | Rohrer et al. | 422/307 |
| 4,980,039 | 12/1990 | Aysola et al. | 204/157.43 |
| 4,994,237 | 2/1991 | Login et al. | 422/21 |
| 4,999,471 | 3/1991 | Guarneri et al. | 219/10.55 M |
| 5,019,344 | 5/1991 | Kutner et al. | 422/21 |
| 5,035,858 | 7/1991 | Held et al. | 422/21 |
| 5,124,125 | 6/1992 | Brent | 422/21 |
| 5,130,092 | 7/1992 | Liu | 422/28 |

FOREIGN PATENT DOCUMENTS

| | | |
|---|---|---|
| 3833281C1 | 3/1990 | Fed. Rep. of Germany . |
| P3924744.9-41 | 1/1991 | Fed. Rep. of Germany . |

OTHER PUBLICATIONS

Nordpunkt AG, Serifant 90 product brochure, Dec. 5, 1990.

ABB Flaekt Sanitec GmbH product brochure, Dec. 5, 1990.

Primary Examiner—Robert J. Warden
Assistant Examiner—L. M. Crawford
Attorney, Agent, or Firm—Richard S. Roberts

[57] ABSTRACT

A process and apparatus for sterilizing bio-active infectious waste matter by a) placing infectious waste in a degradable container, and positioning the container in a pressure vessel; and b) injecting steam into the vessel to wet the container and the infectious waste; and c) subjecting the wet container and infectious waste matter to sufficient microwave radiation to sterilize the waste; and d) heating the sterilized waste matter and container until they are dry; and e) granulating the waste and container to produce small unrecognizable fragment particles.

7 Claims, 4 Drawing Sheets

APPARATUS FOR STERILIZING MEDICAL WASTE BY MICROWAVE AUTOCLAVING

BACKGROUND OF THE INVENTION

The present invention relates to the sterilization of medical waste or more particularly to the sterilization of medical waste by use of a microwave autoclave wherein the waste material is subsequently readied for incineration or landfilling.

Medical waste is infectious refuse that can transmit disease. Medical waste generators include hospitals, doctors' offices, clinics, dental offices, laboratories, nursing homes, and funeral parlors. In addition, as medical costs rise, more long term illnesses are being treated at home and medical waste is thereby being mixed with ordinary household trash. In recent years the amount of medical waste has dramatically increased with the expanded use of disposable rather than reusable products. In addition, in many jurisdictions, the definition of medical waste has been broadened to include an ever widening variety of materials. The Center for Disease Control has issued recommended procedures whereby any material that comes into contact with any patient's body fluids be treated as if it were infectious. Examples of waste materials include bandages, gloves, tubing, syringes, laboratory cultures, and pathological wastes, among others. This waste is isolated in special sealed containers until they can be treated. Except for chemical treatment, all infectious bacteria, viruses and organisms are normally destroyed by some form of heat. The most widely used forms of treatment are autoclaving, or sterilization with steam, and burning at specially equipped incineration sites since most hospital incinerators do not meet pollution control and other regulatory standards. Retrofitting existing hospital incinerators or building new environmentally acceptable incinerators are extremely costly alternatives. On-site, low cost treatment of medical waste is very desirable.

The generally acknowledged most reliable method of sterilization is autoclaving, which entails the heating of items to at least about 212° F. in a steam saturated atmosphere for periods of time ranging from about ten minutes to one day or more. Pressurized steam sterilization of instruments by autoclaving has been done by hospitals and medical offices for many years. However, the microwave autoclave sterilization of disposable medical waste has not been known heretofore. It is clear that large scale sterilization of medical waste is only possible if steam is able to penetrate bagged waste for a sufficient time at a sufficient pressure and temperature to effect essentially complete sterilization. In this regard a pressure vessel is required in order to achieve sterilization process as opposed to a vessel which is open to normal atmospheric conditions. After autoclaving or incineration, residues can be deposited in landfills. Another method of sterilization commonly used is dry heat, however, dry heat sterilization in ovens requires lengthy periods of heating. Other sterilization methods successfully used in limited situations include chemical vapor sterilization, bacteriocidal chemical treatment, and liquid disinfectant usage.

In response to an increase in illegal medical waste disposal, most States have issued statutes and regulations on the handling of medical waste both from large and small scale generators. In addition, the federal Medical Waste Tracking Act created a lifetime tracking system for infectious waste and before sterilized waste can be disposed of as non-infectious waste it must be rendered non-recognizable compared to its original form. The present invention provides a process for sterilizing infectious waste materials by subjecting them to a microwave autoclaving sterilization technique with subsequent granulation. The sterilization renders the waste non-infectious and the grinding yields a product which is non-recognizable as compared to its original form.

Sterilization by use of microwaves is per se known in the art for other applications. It is known that bacteria can be killed using microwaves, and that the effective mechanism by which this is accomplished is not entirely heat dependent. The microwave field effect itself is a contributing mechanism by which sterilization is accomplished. Thus, heating and drying by microwaves provides an advantage that ordinary heating and drying techniques cannot accomplish. In this regard, U.S. Pat. Nos. 3,880,586 and 3,885,915 each show an apparatus for sterilizing sealed, medicinal liquid filled ampules with microwave radiation. U.S. Pat. No. 3,955,286 similarly sterilizes ampules, except microwave irradiation is done in a hermetically sealed pressure vessel. U.S. Pat. No. 3,885,915 shows a method for the destruction of microorganisms in materials such as blood plasma and milk by a combination of ultraviolet and microwave radiation where the temperature is maintained below 100° C. U.S Pat. No. 4,839,142 shows microwave pasteurization of biological fluids where the fluids are subsequently recovered. U.S. Pat. No. 3,955,286 shows sterilizing unfilled ampules using microwave radiation in a sealed vessel with repetitive pressure changes. U.S. Pat. Nos. 4,223,512; 4,250,139; 4,393,088; 4,400,401; 4,406,860; 4,406,861; 4,839,485 and 4,999,471 show microwave sterilization and heating of food and protein material. U.S. Pat. Nos. 4,614,514; 4,599,216; 4,671,935; 4,956,155; 4,971,773 and 5,019,344 show devices for microwave sterilizing items such as dialysis couplings, dentures, dental handpieces and contact lenses. U.S. Pat. No. 4,994,237 shows the microwave preservation of biological tissues such that tissue pliability and the qualities of natural, unpreserved tissue are maintained.

U.S. Pat. No. 4,896,010 shows a method of microwave drying and sanitizing fabrics. In this disclosure, a microwave field effect in combination with confined heated water below the boiling point sanitizes moist, bacteria laden fabrics. U.S. Pat. No. 4,935,114 shows a process for disposing toxic waste including chlorinated hydrocarbons by subjecting them to microwave radiation under conditions sufficient to break the hydrocarbon-chlorine bonds. U.S. Pat. No. 4,980,039 shows the degradation of halogenated hydrocarbon wastes by wet ashing with a reagent of 1:1 nitric acid and sulfuric acid and microwaving. None of these relate to medical waste treatment. U.S. Pat. No. 4,670,227 relates to steam sterilization of medical waste, however, such does not involve microwave irradiation to internally penetrate the waste as described below.

An important feature of any autoclave sterilization process is to provide verification that the waste has been retained at the requisite time and temperature to assure essentially complete sterilization. When using microwave techniques, heat is generated by penetrating and causing a vibration of the internal molecules of the waste. This shortens the time required to reach the temperature needed for sterilization. When non-homogeneous materials are microwave heated in the presence of water vapor, the high frequency provides moisture vaporization and a vapor transport dynamic unique to any other heat source including the simple introduction of steam. In the case of the usual autoclave, steam is introduced but is denied penetration due to mass permeability. As steam contacts the outer layer of the material, it condenses, transferring its thermal energy to the material being heated. It will continue this method of heating material sections from the outside in, as new external steam is applied and as the material permits. In order to revaporize the condensate in-situ, to promote continued internal migration, a method of internal heat dynamic is necessary. Artificial means of forcing steam into the core improve results, but are of limited ability to provide fast, even heat. Properly applied microwave heating provides this unique dynamic for the sterilization of medical waste. Electric field access to internal moisture instantly re-vaporizes condensate, thereby creating a continuous wave of internal steam. It is also known in the art to attempt to sterilize medical waste using microwave energy. In particular German patent application P3924744.9-41 shows a process for sterilizing medical waste where the waste is disposed in a hermetically sealed container, saturated with moisture via injection needles and microwaved in a tunnel. The container is then discharged from the tunnel. In this disclosure, sterilization occurs inside sealed plastic containers and not in a pressurized microwave chamber. This system is disadvantageous since the plastic container can degrade, melt or break and release the internal pressure and contaminate the inside of the chamber where the container is placed. In addition, if the pressure in the plastic container releases, sterilization conditions can no longer be insured. German patent 3833281 C1 shows a hermetically sealable waste container useful in the aforesaid process. Such a system is commercially available as Serifant 90 from Nordpunkt AG. This system does not provide means for granulating the medical waste and the container so that it is rendered unrecognizable and suitable for disposal as non-infectious material.

In a sterilization system commercially available from ABB Flaekt Sanitec GmbH, medical waste is first shredded, steam is introduced to supply moisture to the dry waste and then the waste proceeds along a screw where microwave energy is applied supposedly to complete sterilization. However, this method is disadvantageous because medical waste that is shredded before treatment can release airborne infectious organisms. Also, infected waste contaminates the shredders, augers and other internal parts of the machinery thereby preventing safe equipment maintenance. In addition, this open system does not contain steam in a pressure vessel so that a temperature sufficient for sterilization cannot be reached or maintained. This method is actually a system for disinfection, which is an incomplete sterilization. In addition, disinfection verification can only be done by sampling the material. A test vial of spores is introduced which can indicate whether the process was effective, but only after a twenty-four hour waiting period. This delay is impractical and does not allow the treated waste to be immediately taken away for incineration or landfilling.

This invention provides improved method for sterilizing medical waste by converting it into non-infectious material which is non-recognizable from its original form. This treated waste can then be disposed of much less expensively as ordinary trash such as by landfilling or burning in normal incinerators. The invention provides a process wherein medical waste is disposed in individual degradable containers, preferably composed of cardboard. The waste filled containers are positioned in a pressure vessel into which steam is injected. The vessel is then subjected to microwave radiation for a sufficient time and at a sufficient temperature and pressure to effect essentially complete sterilization of the waste and the container. In a subsequent step, both the waste and the container are shredded and/or granulated so as to render the product and container unrecognizable compared to the original items. Indicia are provided whereby sterilization is verified for each bag or individual container and a manifest is printed out to provide assurance that the required conditions were met to effect sterilization. The vessels are modular and can be ganged together to provide the desired throughput volume.

SUMMARY OF THE INVENTION

The invention provides a process for sterilizing bio-active infectious waste matter comprising in order:

a) disposing infectious waste matter in a degradable container, and positioning the container within a vessel, which vessel is capable of sustaining pressures at, below and in excess of atmospheric pressures; and b) injecting sufficient steam into said vessel to wet said container and at least a portion of said infectious waste matter and to provide a steam saturated atmosphere; and c) subjecting said container and infectious waste matter to sufficient microwave radiation for a sufficient time, and at a sufficient temperature and at a sufficient pressure to substantially sterilize said waste matter; and d) subjecting said sterilized waste matter and said container to a treatment for a sufficient time, and at a sufficient temperature until they are substantially dry.

The invention further provides an apparatus for sterilizing bio-active infectious waste matter comprising:

a) a vessel capable of enveloping a degradable container, which container is capable of retaining infectious waste matter therein; said vessel being capable of sustaining pressures at and in excess of atmospheric pressures; and b) means for injecting steam into said vessel in an amount sufficient to wet said container and at least a portion of said infectious waste matter when such are disposed therein and to provide a steam saturated atmosphere therein; and c) means for subjecting a container and infectious waste matter when disposed within said vessel to sufficient microwave radiation for a sufficient time and at a sufficient temperature and at a sufficient pressure to substantially sterilize said waste matter; and d) means for drying said sterilized waste matter and said container for a sufficient time and at a sufficient temperature until they are substantially dry.

The invention still further provides an apparatus for sterilizing bio-active infectious waste matter comprising:

a) a vessel having mating front, rear and side walls forming a hollow inner compartment, which is preferably square, rectangular or round, said vessel having an open top capable of accepting a degradable container therethrough, which container is capable of retaining infectious waste matter therein; said vessel having a hinged floor at its bottom capable of alternately sealing the bottom of said vessel when the floor is in a closed position and allowing the contents of the vessel to fall through the bottom of the vessel when the floor is in the open position; said vessel being capable of sustaining pressures at and in excess of atmospheric pressures; and b) a pressure chamber capable of receiving the inner compartment of the vessel, said chamber having top, bottom, rear and side walls;

c) said vessel being mounted on sliding means which sliding means allow said compartment to be alternatively positioned within the pressure chamber, which pressure chamber is sealed by the front wall of the vessel when in a closed position, and outside the pressure chamber when in the open position, allowing an insertion of a degradable container through the open top of said vessel compartment; the bottom of said vessel being sealed closed by said floor when the vessel is in the pressure chamber and being capable of being opened when the vessel is outside the pressure chamber; and d) means for injecting steam into said vessel in an amount sufficient to wet a degradable container and at least a portion of infectious waste matter when such are disposed in said vessel and to provide a steam saturated atmosphere therein; and e) means for subjecting a wet container and wet infectious waste matter disposed within said vessel to sufficient microwave radiation heating for a sufficient time and at a sufficient temperature and at a sufficient pressure to substantially sterilize said waste matter; and d) means for drying said sterilized waste matter and said container for a sufficient time and at a sufficient temperature until they are substantially dry.

DETAILED DESCRIPTION OF THE PREFERRED EMBODIMENT

Figure 1:
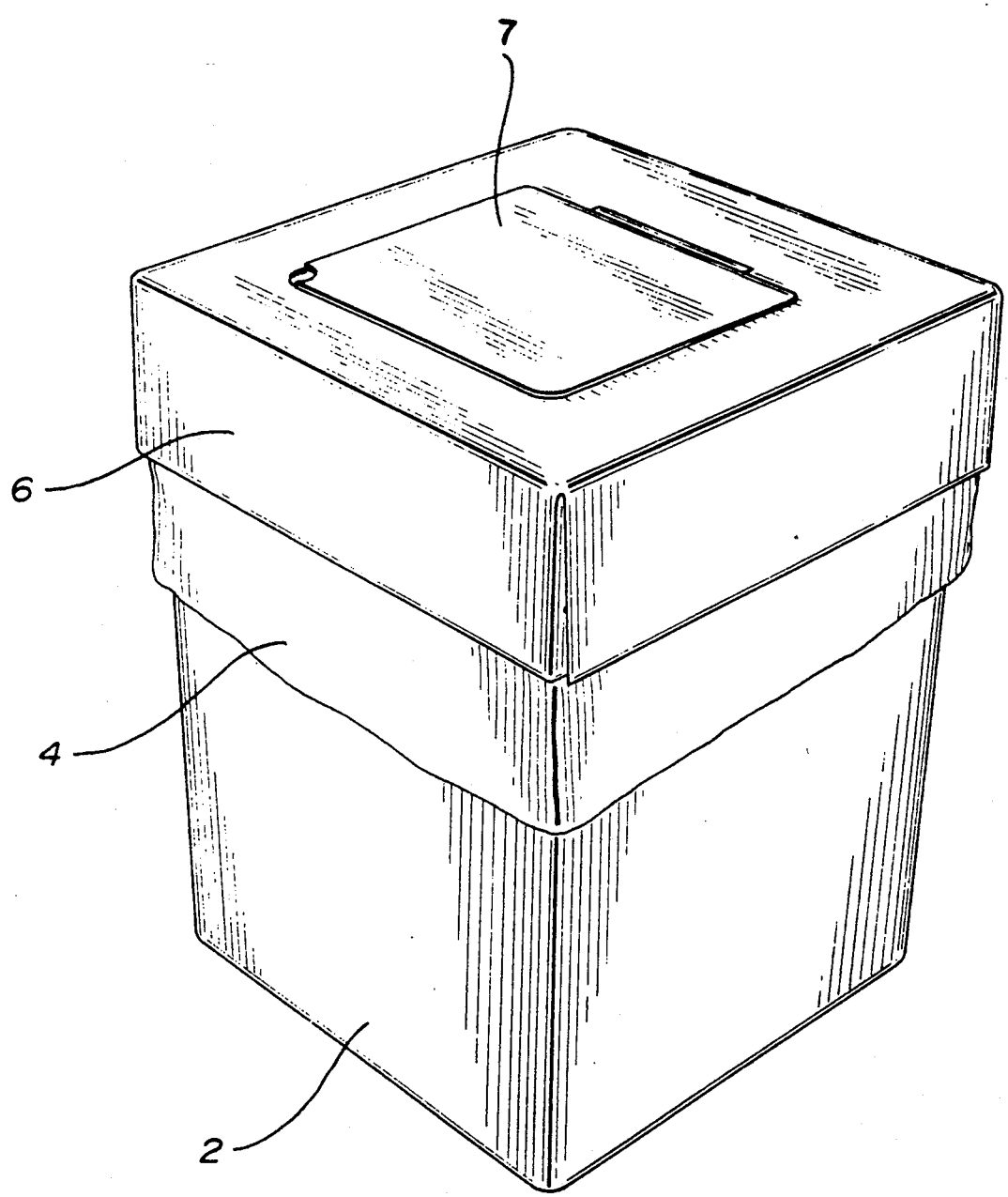
FIG. 1 shows a cardboard container suitable for the collection of infectious waste.
Figure 2:
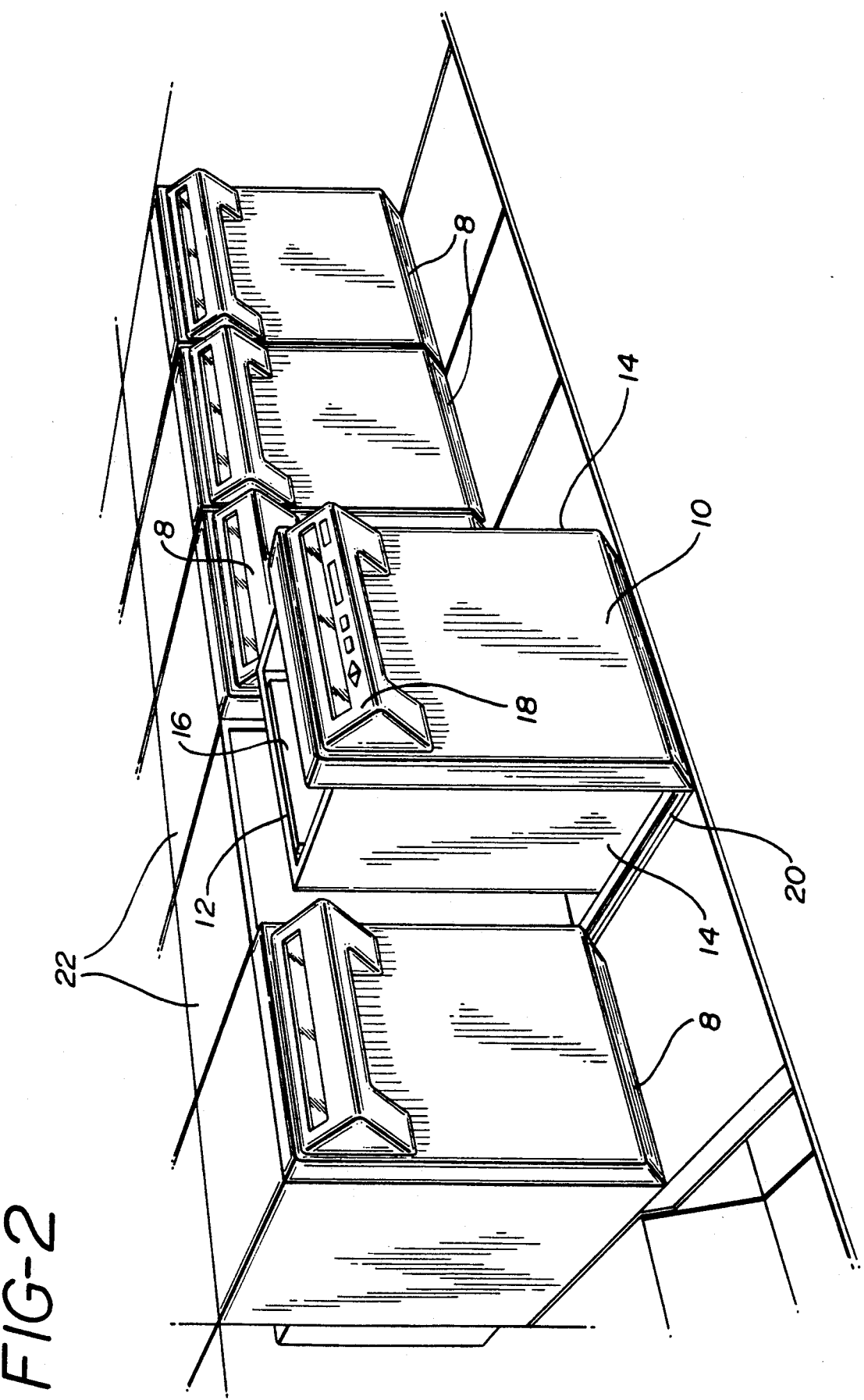
FIG. 2 shows a series of ganged autoclaving vessels suitable for receiving a degradable container filled with infectious waste.

In the process for sterilizing bio-active infectious waste matter the infectious waste is first disposed of by the waste generator into a degradable container. In the preferred embodiment, the container is moisture absorbing or breaks up in the presence of moisture. Biodegradable materials may be used and in the most preferred embodiment the container is composed of a material such as corrugated cardboard and the like. Referring now to FIG. 1, there is shown cardboard container suitable for the collection of infectious waste. The container comprises a hollow, relatively cubical base 2 which is preferably lined with a resilient plastic bag 4. The container is provided with a lid 6 which can optionally be provided with means to fasten it to the base 2. In the preferred embodiment, the top has a hinge type access port 7 so that users can merely raise the port to dispose of waste rather than being required to remove the entire lid 6. This port can then be sealed shut for transportation. In use, the container is positioned in an autoclaving vessel 8, a ganged group of which are depicted in FIG. 2. The vessel has mating front, rear and side walls respectively 10, 12 and 14, forming a hollow, substantially rectangular inner compartment 16. The vessel has an open top capable of accepting a degradable container such as that shown in FIG. 1 inside of it. The vessel is provided with a suitable control panel 18 for controlling the operation of the apparatus as well as indicating the status of the process steps. In the preferred embodiment, the control panel has means and indicia for printing out and/or otherwise recording the time, temperature, pressure and microwave radiation applied during the operation of the apparatus and appropriate probes may be positioned within the vessel during operation. The controls for these parameters are interlocked through a programmable logic controller which are well known in the art. It additionally may have means for measuring the bio-activity of waste matter contained in the vessel and determining whether said waste matter is substantially sterilized. In one embodiment of the invention, the process parameters can be verified by providing suitable temperature, pressure and time measuring devices within the pressure chamber. In another embodiment of the invention, the user can employ a known, one time use, disposable measuring device placed within the vessel during processing which assures that the desired temperature, pressure and time parameters are achieved.

Figure 3:
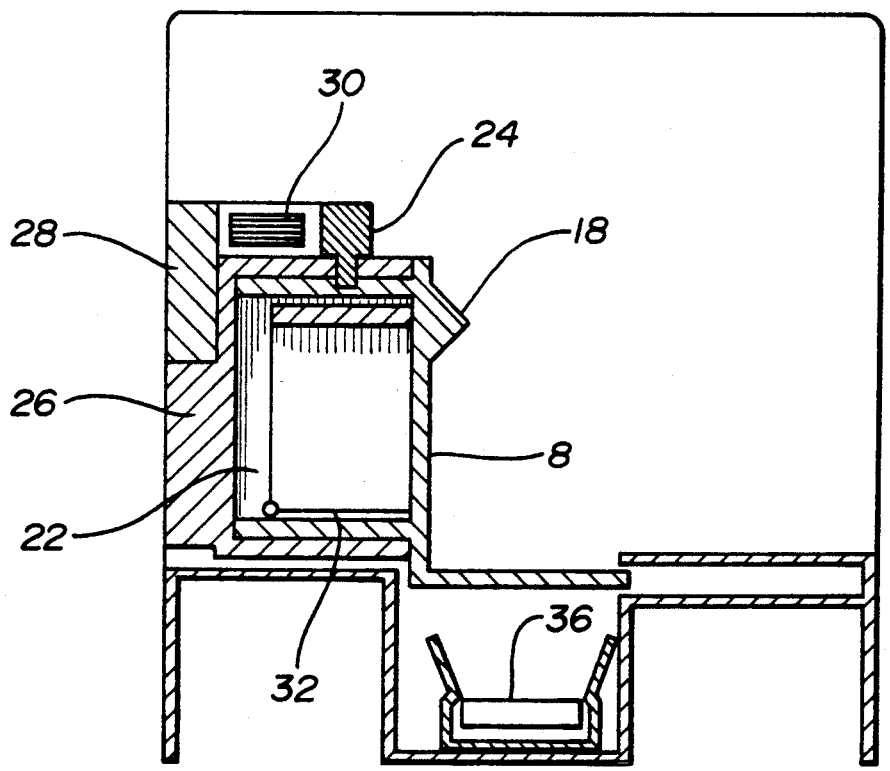
FIG. 3 schematically shows an apparatus for sterilizing infectious waste according to the invention with a vessel in the closed position, ready for sterilization.

As shown in FIG. 2, the vessel is capable of sliding via suitable slide means 20 into and out of a pressure chamber 22 which is capable of sustaining pressures at, below and in excess of atmospheric pressures. FIG. 2 shows one vessel in the open position and four additional vessels in the closed position, i.e. within their respective pressure chambers. FIG. 3 schematically shows vessel 8 in the closed position within pressure chamber 22. The apparatus has a steam dosing lance 24 capable of piercing the container and injecting sufficient steam into the vessel to wet the container and preferably also at least a portion of the infectious waste matter and to provide a steam saturated atmosphere in the vessel. The ambient air in the vessel which may be vented at this point is potentially infectious. This can be captured in a gas bottle and reinjected into the vessel in a closed system.

Figure 4:
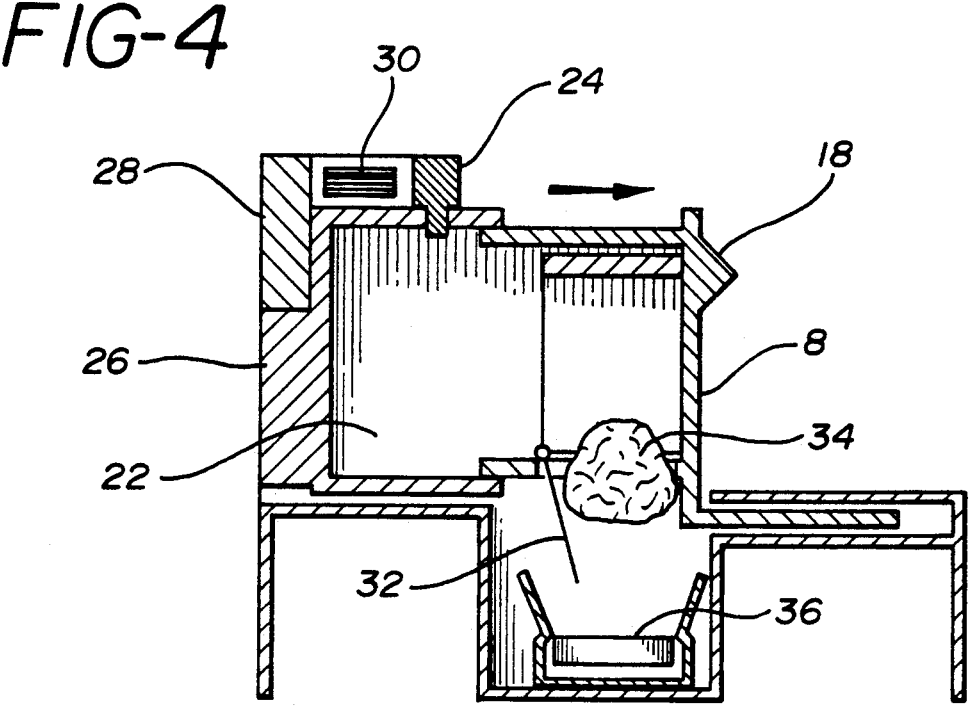
FIG. 4 schematically shows an apparatus for sterilizing infectious waste according to the invention with a vessel in the open position after sterilization.

The apparatus has a microwave generator 26 capable of subjecting the wet container and infectious waste matter to sufficient microwave radiation for a sufficient time, and at a sufficient temperature and at a sufficient pressure to substantially sterilize the infectious matter. In an alternate embodiment, the apparatus has a steam generator 28 which can assist in the autoclaving process. After sterilization, the treated mass in the vessel is heated by microwaving until it is substantially dry. In addition, the moist waste can be tumbled for drying within the vessel which is disposed within the pressure chamber. The microwaves penetrate the waste, causing the moisture within the mass to evaporate. A portion of the moisture in the vessel can be removed from the sterilized mass before or during the drying procedure. During the sterilization and heating steps a considerable amount of pressure can build up. Prior to opening the vessel, the chamber is vented and sterilized air passes through vented filter 30. After the foregoing steps are complete, the vessel can be opened for removal of the treated waste mass and readying for the next batch. As best seen in FIG. 4, vessel 8 opens by sliding it out of pressure chamber 22 in the direction of the arrow. In one embodiment, the waste is removed out of the top of the vessel, however in the preferred embodiment, the vessel is provided with a hinged floor 32, upon the opening of which, sterilized waste mass 34 drops through the floor of the vessel onto conveyor means 36. Hinged floor 32 is capable of alternately sealing the bottom of the vessel when the floor is in a closed position, and allowing the contents of the vessel to fall through the bottom of the vessel when the floor is in the open position.

Figure 5:
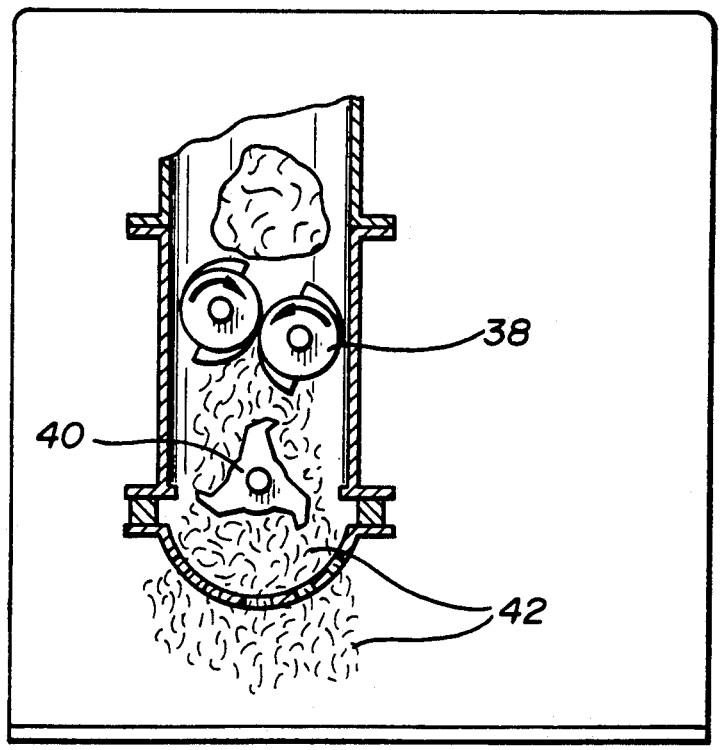
FIG. 5 shows a schematic representation of a shredding and granulating device for the practice of the invention.

As shown in FIG. 5, the conveyor then delivers the treated waste mass to shredder 38 and/or granulator 40 to produce waste fragments 42 which are unrecognizable as compared to their original form, for example, fragments having a particle size of about 1 cm$^2$ or less. These waste fragments 42 are then collected and treated as normal municipal, i.e. non-infectious waste, and can be burned in standard incinerators or landfilled.

The sterilization step is conducted by applying microwave radiation to the degradable container and the infectious medical waste contents for a sufficient time, and at a sufficient temperature and at a sufficient pressure to substantially sterilize the waste matter. As is well known, microwave energy is the electromagnetic wave energy falling in the microwave region of the electromagnetic spectrum. Permitted bands of microwave energy are generally in the range of about 200 to 20,000 megacycles per second with a wavelength ranging from about 13" for the lower frequency to about 0.7" for the highest frequency; narrow bands which find frequent application include frequencies of about 890-940 with a wavelength of about 13"; frequencies of about 2,400-2,500 with a wavelength of about 4-5", and frequencies of about 17,850 to 18,000 with a wavelength of about 0.7". However, for the most part, the microwave energies employed will be in the intermediate range of from about 850 to about 3,000, more usually from about 850 to about 950 or 2,000 to about 3,000 megacycles per second. Microwave energy is generated from a suitable high frequency source, such as a Magnetron or Klystron. Various applicators may be employed for providing microwave energy, such as a resonator, wave guide applicator, or standing wave applicator.

In the preferred embodiment, the sterilization step is conducted at a temperature of at least 212° F. and is more preferably at least about 250° F. A most preferred range is from about 250° F. to about 300° F., although higher temperatures can also be employed. The provision of moisture is important since an enhanced sterilization effect is obtained. Infectious organisms are more easily killed by the combination of the microwave field effect and the accumulated and heated steam which is within the heating vessel. The microwave field effect in combination with the confined, heated water vapor provides enhanced sterilization. When the vaporized moisture is allowed to remain and be further heated within the heating vessel, the microwave field effect in combination with the heated vaporized steam causes a sterilization of the waste. The sterilization method and apparatus utilize both a microwave field effect and heated steam to kill microorganisms. The portion of the microwave heating cycle in which the sterilization is accomplished is at the beginning thereof after which, the mass can be further heated with or without application of a conventional airflow to complete the drying process. It is also contemplated by this invention that there can be a sterilization cycle at an end portion of the microwave heating cycle, in order to kill any air-borne contaminants introduced by any subsequent drying airflow. It is also contemplated that the sterilized dry airflow can be adequately filtered to prevent the introduction of foul odors.

In the preferred embodiment, the sterilization step is conducted at a pressure of from a point above atmospheric pressure to about 100 psig, or more preferably from about 3 psig to about 85 psig, and most preferably from about 15 psig to about 50 psig.

The time for the treatment will vary depending upon the type and density of the waste material and the degree of sterilization assurance desired. In the preferred embodiment, the sterilization step is conducted for from at least about 10 minutes or more preferably from about 15 minutes to about 120 minutes, and most preferably from about 15 minutes to about 30 minutes. The time will also vary with the frequency of the microwave radiation, and the power output of the Magnetron. For the most part, the microwave energy density inside the processing cavity will be up to about 0.025 mW/cm$^3$, and usually above about 0.001 mW/cm$^3$. In one most preferred embodiment, the sterilization step is conducted at a temperature of about 250° F., at a pressure of about 15 psig for about 30 minutes. The process of can be repeated again by repeating the steam injection, sterilizing and drying steps when a measuring step indicates that the waste matter is not sufficiently sterilized.

It is understood that the foregoing pertains to the preferred embodiments of the invention, it being understood that other embodiments and variants thereof are possible within the spirit and scope of the invention.

What is claimed is:

1. An apparatus for sterilizing infectious waste matter comprising:
   a) a vessel having mating front, rear and side walls forming a hollow inner compartment, said vessel having an open top capable of accepting a degradable container therethrough, which container is capable of retaining infectious waste matter therein; said vessel having a hinged floor at its bottom capable of alternately sealing the bottom of said vessel when the floor is in a closed position and allowing the contents of the vessel to fall through the bottom of the vessel when the floor is in the open position; said vessel being capable of sustaining pressures at and in excess of atmospheric pressures; and
   b) a pressure chamber capable of receiving the inner compartment of the vessel, said chamber having top, bottom, rear and side walls;
   c) said vessel being mounted on sliding means which sliding means allow said compartment to be alternatively positioned within the pressure chamber, which pressure chamber is sealed by the front wall of the vessel when in a closed position, and outside the pressure chamber when in the open position, allowing an insertion of a degradable container through the open top of said vessel compartment; the bottom of said vessel being sealed closed by said floor when the vessel is in the pressure chamber and being capable of being opened when the vessel is outside the pressure chamber; and
   d) means for injecting steam into said vessel in an amount sufficient to wet a degradable container and at least a portion of infectious waste matter when such are disposed in said vessel and to provide a steam saturated atmosphere therein; and e) means for subjecting a wet container and wet infectious waste matter disposed within said vessel to sufficient microwave radiation heating for a sufficient time and at a sufficient temperature and at a sufficient pressure to sterilize said waste matter; and f) means for drying said sterilized waste matter and said container for a sufficient time and at a sufficient temperature until they are dry.

2. The apparatus of claim 1 further comprising means for subsequently subjecting said sterilized waste matter and said container to one or more treatments selected from the group consisting of shredding and granulating to thereby provide fragments having an average particle size of about 1 cm$^2$ or less.

3. The apparatus of claim 2 further comprising means for incinerating said fragments.

4. The apparatus of claim 2 further comprising means for conveying said waste matter to said shredding and/or granulating means.

5. The apparatus of claim 1 further comprising means for measuring the infectiousness of said waste matter and determining whether said waste matter is sterilized.

6. The apparatus of claim 1 comprising means for recording the time, temperature, pressure and microwave radiation used during the operation of the apparatus.

7. The apparatus of claim 1 wherein said means for injecting steam comprises a steam dosing lance which is capable of piercing and wetting both said container and said infectious waste matter.

* * * * *